United States Patent
Vaysse-Ludot et al.

(10) Patent No.: US 7,238,815 B2
(45) Date of Patent: Jul. 3, 2007

(54) PROCESS FOR THE INDUSTRIAL SYNTHESIS OF THE METHYL DIESTER OF 5-AMINO-3-CARBOXYMETHYL-4-CYANO-2-THIOPHENECARBOXYLIC ACID, AND APPLICATION TO THE SYNTHESIS OF BIVALENT SALTS OF RANELIC ACID AND THEIR HYDRATES

(75) Inventors: Lucile Vaysse-Ludot, Saint-Wandrille-Rancon (FR); Jean-Pierre Lecouve, le Havre (FR); Pascal Langlois, Saint Jean de la Neuville (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/358,496

(22) Filed: Feb. 21, 2006

(65) Prior Publication Data
US 2006/0142596 A1  Jun. 29, 2006

Related U.S. Application Data

(62) Division of application No. 10/669,738, filed on Sep. 24, 2003, now Pat. No. 7,105,683.

(30) Foreign Application Priority Data
Sep. 24, 2002  (FR) ................... 02 11764

(51) Int. Cl.
*C07D 333/42*  (2006.01)

(52) U.S. Cl. ........................................ 549/63

(58) Field of Classification Search ................... 549/63
See application file for complete search history.

(56) References Cited

FOREIGN PATENT DOCUMENTS
EP  0415850  3/1991

OTHER PUBLICATIONS

Synthesis of 2-azo-3-cyano-5-carbethoxy thiophene derivatives and their application on polyester fibers. Journal of Chemical Technology and Biotechnology (1990), 47(1), 39-46 CAS Abstract Only.*
French Search Report for French Application No. 02.11764, Apr. 1, 2003.
International Preliminary Examination Report for International No.PCT/FR2003/002776, Dec. 3, 2004.
Wierzbickie, et al., *Bull. Chim. Soc. Fr.*, 1975, 7-8 1786-1792.

* cited by examiner

*Primary Examiner*—Kamal A. Saeed
(74) *Attorney, Agent, or Firm*—Hueschen and Sage

(57) ABSTRACT

Process for the industrial synthesis of the compound of formula (I):

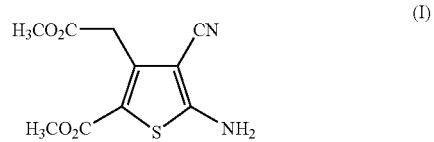

Application to the synthesis of bivalent salts of ranelic acid and more especially strontium ranelate and its hydrates.

1 Claim, No Drawings

PROCESS FOR THE INDUSTRIAL SYNTHESIS OF THE METHYL DIESTER OF 5-AMINO-3-CARBOXYMETHYL-4-CYANO-2-THIOPHENECARBOXYLIC ACID, AND APPLICATION TO THE SYNTHESIS OF BIVALENT SALTS OF RANELIC ACID AND THEIR HYDRATES

This application is a Divisional of U.S. application Ser. No. 10/669,738 filed Sep. 24, 2003, now U.S. Pat. No. 7,105,683, which claims priority under 35 U.S.C. 119 FRANCE FR 02.11764 filed Sep. 24, 2002.

The present invention relates to a process for the industrial synthesis of the methyl diester of 5-amino-3-carboxymethyl-4-cyano-2-thiophenecarboxylic acid and to the application thereof in the industrial production of bivalent salts of ranelic acid and their hydrates.

More specifically, the present invention relates to a new process for the industrial synthesis of the compound of formula (I):

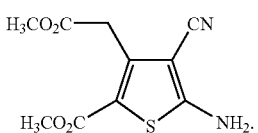

The compound of formula (I) obtained according to the process of the invention is useful in the synthesis of ranelic acid, its strontium, calcium or magnesium salts of formula (II):

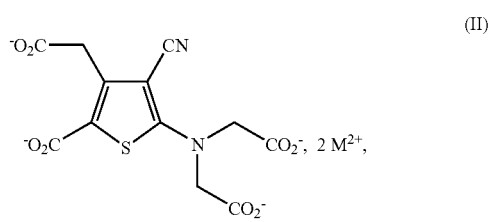

wherein M represents strontium, calcium or magnesium, and hydrates of the said salts.

BACKGROUND OF THE INVENTION

The bivalent salts of ranelic acid have very valuable pharmacological and therapeutic properties, especially pronounced anti-osteoporotic properties, making these compounds useful in the treatment of bone diseases.

DESCRIPTION OF THE PRIOR ART

The bivalent salts of ranelic acid, and more especially strontium ranelate, the preparation thereof and the therapeutic use thereof have been described in the European Patent Specification EP 0 415 850.

That Patent Specification describes the synthesis of strontium ranelate starting from the ethyl tetraester of formula (III):

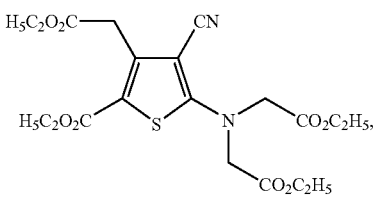

which is itself obtainable starting from the ethyl diester of formula (IV):

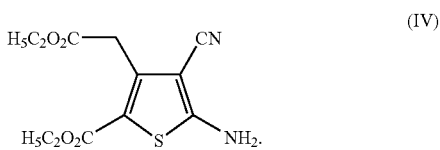

Synthesis of the intermediate of formula (IV) has been described in the publication Bull. Soc. Chim. France 1975, pp. 1786-1792 and in the publication J. Chem. Tech. Biotechnol. 1990, 47, pp. 39-46, by reaction between diethyl 3-oxoglutarate, malononitrile and sulphur in ethanol, in the presence of morpholine or diethylamine.

That process has the advantage of using readily accessible starting materials and of being simple to put into practice; however, when transferred to the scale of several hundred kilograms, it does not allow the compound of formula (IV) to be obtained in a yield greater than 70%.

In view of the pharmaceutical interest of strontium ranelate and the tonnages produced, it has been important to be able to synthesise a diester of 5-amino-3-carboxymethyl-4-cyano-2-thiophenecarboxylic acid of excellent purity, in a yield of at least 77%, which is reproducible on an industrial scale.

DETAILED DESCRIPTION OF THE INVENTION

The Applicant has now developed an effective industrial synthesis process allowing the methyl diester of formula (I) to be obtained in a yield of at least 77% and with a purity greater than 97%.

The compound of formula (I) thereby obtained is especially useful in the synthesis of ranelic acid, its strontium, calcium or magnesium salts and hydrates of the said salts, more especially strontium ranelate and its hydrates, wherein it is reacted with an ester of bromoacetic acid to yield the corresponding tetraester, which is then converted into ranelic acid or into a strontium, calcium or magnesium salt thereof.

More specifically, the present invention relates to a process for the industrial synthesis of the compound of formula (I), which process is characterised in that dimethyl 3-oxoglutarate of formula (V):

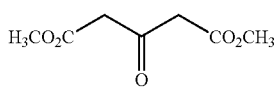
(V)

is reacted with malonitrile of formula (VI):

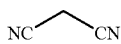
(VI)

in methanol,
in the presence of morpholine in an amount greater than 0.95 mol per mol of compound of formula (V),
to yield the compound of formula (VII):

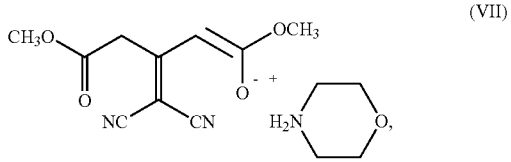
(VII)

which is then reacted with sulphur in an amount greater than 0.95 mol per mol of compound of formula (V);
the reaction mixture is then heated at reflux;
and the compound of formula (I) thereby obtained is isolated by precipitation in the presence of water, followed by filtration.

The process, accordingly improved by the use of these very specific conditions, and especially by the intermediate formation of the compound of formula (VII), which can, if desired, be isolated, allows the compound of formula (I) to be obtained with excellent purity and in a yield of at least 77% which is reproducible on the scale of several hundred kilograms, which represents a major gain in yield in view of the large tonnages of strontium ranelate produced.

The amount of methanol is preferably from 1 to 3 ml per gram of compound of formula (V).

The temperature of reaction between the compounds of formulae (V) and (VI) is preferably less than 50° C.

The reaction time at reflux after addition of the sulphur is preferably from 1 hour 30 minutes to 3 hours.

Methyl 5-amino-4-cyano-3-(2-methoxy-2-oxoethyl)-2-thiophenecarboxylate of formula (I) and the intermediate of formula (VII) are new compounds which are useful as synthesis intermediates in the chemical or pharmaceutical industry, especially in the synthesis of strontium ranelate, and accordingly form an integral part of the present invention.

The Examples hereinbelow illustrate the invention but do not limit it in any way.

EXAMPLE 1

Methyl 5-amino-4-cyano-3-(2-methoxy-2-oxoethyl)-2-thiophenecarboxylate

Introduce into a reactor 400 kg of dimethyl 3-oxoglutarate, 158 kg of malononitrile and 560 liters of methanol and then, whilst maintaining the temperature of the reaction mixture below 40° C., 199.6 kg of morpholine.

Then introduce 73.6 kg of sulphur and subsequently bring the mixture to reflux.

After reacting for 2 hours, stop refluxing and add water until precipitation occurs. Filter off the precipitate obtained, wash it and dry it.

Methyl 5-amino-4-cyano-3-(2-methoxy-2-oxoethyl)-2-thiophenecarboxylate is thereby obtained in a yield of 77% and with a chemical purity of 98%.

EXAMPLE 2

Methyl 5-amino-4-cyano-3-(2-methoxy-2-oxoethyl)-2-thiophenecarboxylate

Introduce into a reactor 400 kg of dimethyl 3-oxoglutarate, 158 kg of malononitrile and 560 litres of methanol and then, whilst maintaining the temperature of the reaction mixture below 40° C., 199.6 kg of morpholine.

The compound of formula (VII) thereby obtained, or the addition salt of methyl 3-(dicyanomethylene)-5-hydroxy-5-methoxy-4- pentenoate with morpholine, is isolated by filtration after cooling of the mixture and is then reacted with 73.6 kg of sulphur in methanol.

The mixture is then brought to reflux.

After reacting for 2 hours, stop refluxing and add water until precipitation occurs. Filter off the precipitate obtained, wash it and dry it.

We claim:

1. A process for the synthesis of ranelic acid, its strontium, calcium or magnesium salts and hydrates of the salts, starting from a compound of formula (I):

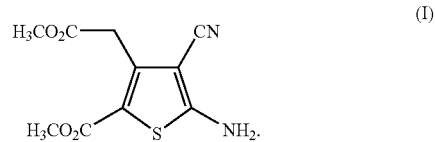
(I)

which is reacted with an ester of bromoacetic acid to yield the corresponding tetraester, which is converted into ranelic acid or a strontium, calcium or magnesium salt thereof via hydrolysis in the presence of sodium hydroxide, the product of which reaction is either treated with strontium hydroxide, calcium hydroxide or magnesium hydroxide, or subjected to further hydrolysis in the presence of acid followed by treatment with strontium chloride, calcium chloride, or magnesium chloride.

* * * * *